(12) United States Patent
Devic et al.

(10) Patent No.: US 8,329,964 B2
(45) Date of Patent: Dec. 11, 2012

(54) METHOD FOR PREPARING 2,3,3,3-TETRAFLUORO-1-PROPENE

(75) Inventors: Michel Devic, Sainte Foy les Lyon (FR); Dominique Guillet, Vernaison (FR); Emmanuel Guiraud, Saint-Genis Laval (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 282 days.

(21) Appl. No.: 12/665,140

(22) PCT Filed: Mar. 27, 2009

(86) PCT No.: PCT/IB2009/005095
§ 371 (c)(1),
(2), (4) Date: Apr. 21, 2010

(87) PCT Pub. No.: WO2009/118632
PCT Pub. Date: Oct. 1, 2009

(65) Prior Publication Data
US 2010/0305370 A1 Dec. 2, 2010

(30) Foreign Application Priority Data
Mar. 28, 2008 (FR) .................................... 08 01727

(51) Int. Cl.
*C07C 17/23* (2006.01)
(52) U.S. Cl. ...................................................... 570/156
(58) Field of Classification Search .................. 570/156
See application file for complete search history.

(56) References Cited

U.S. PATENT DOCUMENTS

| 4,902,838 | A | 2/1990 | Manzer et al. |
| 5,396,000 | A | 3/1995 | Nappa et al. |
| 5,679,875 | A | 10/1997 | Aoyama et al. |
| 2009/0127496 | A1 | 5/2009 | Rao et al. |
| 2009/0264689 | A1 | 10/2009 | Rao et al. |

FOREIGN PATENT DOCUMENTS

| EP | 486333 | 5/1992 |
| WO | WO 2007/056194 | 5/2007 |
| WO | WO 2008/030440 | 3/2008 |

OTHER PUBLICATIONS

Knunyants et al., Journal of the USSR Academy of Sciences, Chemistry Department, "Reactions of Fluoroolefins", report 13, "Catalytic Hydrogenation of Perfluoroolefins", 1960.

*Primary Examiner* — Rebecca Anderson
*Assistant Examiner* — Samantha Shterengarts
(74) *Attorney, Agent, or Firm* — Steven D. Boyd

(57) ABSTRACT

The invention relates to a gas-phase continuous method for preparing 2,3,3,3-tetrafluoro-1-propene, said method comprising the following steps: (i) hydrogenation of hexafluoropropylene to form 1,1,1,2,3,3-hexafluoropropane; (ii) dehydrofluorination of the 1,1,1,2,3,3-hexafluoropropane obtained in the previous step to 1,2,3,3,3-pentafluoropropene-1; (iii) hydrogenation of the 1,2,3,3,3-pentafluoropropene-1 obtained in the previous step to form 1,1,1,2,3-pentafluoropropane; and (iv) dehydrofluorination of the 1,1,1,2,3-pentafluoropropane obtained in the previous step to form 2,3,3,3-tetrafluoro-1-propene.

21 Claims, No Drawings

METHOD FOR PREPARING 2,3,3,3-TETRAFLUORO-1-PROPENE

FIELD OF THE INVENTION

The invention relates to a process for preparing fluorine compounds, namely the fluorine compound 1234yf.

TECHNICAL BACKGROUND

Hydrofluorocarbons (HFC) and in particular hydrofluoro-olefins such as 2,3,3,3-tetrafluoro-1-propene (HFO 1234yf) are compounds that are known for their properties as refrigerants and heat exchangers, extinguishers, propellants, foaming agents, swelling agents, dielectric gases, polymerization or monomer medium, support fluids, abrasive agents, drying agents and fluids for power production units. Unlike CSCs and HCFCs, which are potentially hazardous to the ozone layer, HFOs do not contain chlorine and therefore pose no problem to the ozone layer.

Several processes for manufacturing 1234yf are known.

WO 2008/002 499 describes a process for producing a mixture of 2,3,3,3-tetrafluoro-1-propene (HFO 1234yf) and 1,3,3,3-tetrafluoro-1-propene (HFO 1234ze) by pyrolysis of 1,1,1,2,3-pentafluoropropane (HFC 245eb).

WO 2008/002 500 describes a process for producing a mixture of 2,3,3,3-tetrafluoro-1-propene (HFO 1234yf) and 1,3,3,3-tetrafluoro-1-propene (HFO 1234ze) via catalytic conversion of 1,1,1,2,3-pentafluoropropane (HFC 245eb) on a dehydrofluorination catalyst.

These two abovementioned patent applications are thus directed toward the production of a mixture containing a substantial portion of the product 1234ze.

WO 2007/056 194 describes the preparation of 1234yf by dehydrofluorination of 245eb, especially on a catalyst based on nickel, carbon or a combination of the two.

The document Knunyants et al., Journal of the USSR Academy of Sciences, Chemistry Department, "Reactions of fluoro-olefins", report 13, "Catalytic hydrogenation of per-fluoro-olefins", 1960, distinctly describes various chemical reactions on fluorine compounds. Said document describes the substantially quantitative hydrogenation of HFP on a platinum-supported palladium-based catalyst, the temperature rising from 20° C. to 50° C., and then being maintained at this value. Said document describes the dehydrofluorina-tion of 1,1,1,2,3,3-hexafluoropropane (236ea) via passage through a suspension of KOH, to produce 1,2,3,3,3-pentafluoro-1-propene (1225ye). Said document describes the hydrogenation of 1,2,3,3,3-pentafluoro-1-propene (1225ye) to 1,1,1,2,3-pentafluoropropane (245eb) on an alumina-supported palladium catalyst. During this hydrogenation, a hydrogenolysis reaction also takes place, a significant amount of 1,1,1,2-tetrafluoropropane being produced. Said document describes the dehydrofluorination of 1,1,1,2,3-pentafluoropropane (245eb) to 2,3,3,3-tetrafluoro-1-propene (HFO 1234yf) via passage through a suspension of KOH. These reactions are described independently of each other, although it is indicated that it is possible to combine them to synthesize a range of ethylene, propylene and isobutylene derivatives containing variable amounts of fluorine.

Document U.S. Pat. No. 5,396,000 describes the preparation of 1,1,1,2,3-pentafluoropropane by catalytic dehydrofluorination of 1,1,1,2,3,3-hexafluoropropane (236ea) to 1,2,3,3,3-pentafluoro-1-propene (1225ye), followed by hydrogenation to produce the desired compound. The dehydrohalogenation of 236ea to 1225ye is performed in the gas phase, the reaction product being, in one example, sent directly to the next reactor in which the hydrogenation of the compound 1225ye to the compound 245eb takes place. It is also indicated in that document that the compound 236ea may be obtained by hydrogenation of hexafluoropropylene (HFP), making reference to the abovementioned Knunyants et al. document.

Document U.S. Pat. No. 5,679,875 describes the preparation of 1,1,1,2,3-pentafluoropropane by catalytic dehydrofluorination of 1,1,1,2,3,3-hexafluoropropane (236ea) to 1,2,3,3,3-pentafluoro-1-propene (1225ye), followed by a hydrogenation to produce the desired compound. The reactions are performed in the gas phase. It is also indicated in that document that the compound 236ea may be obtained by hydrogenation of hexafluoropropylene (HFP), making reference, inter alia, to the abovementioned Knunyants et al. document.

There is a need for a process for preparing 1234yf from a readily accessible starting material, and which leads to the desired product in high selectivity, and advantageously in high yield.

SUMMARY OF THE INVENTION

The invention thus provides a continuous gas-phase process for preparing 2,3,3,3-tetrafluoro-1-propene, comprising the following steps:
(i) hydrogenation of hexafluoropropylene to 1,1,1,2,3,3-hexafluoropropane;
(ii) dehydrofluorination of the 1,1,1,2,3,3-hexafluoropropane obtained in the preceding step to 1,2,3,3,3-pentafluoro-1-propene;
(iii) hydrogenation of the 1,2,3,3,3-pentafluoro-1-propene obtained in the preceding step to 1,1,1,2,3-pentafluoropropane;
(iv) dehydrofluorination of the 1,1,1,2,3-pentafluoropropane obtained in the preceding step to 2,3,3,3-tetrafluoro-1-propene.

According to certain embodiments:
the hydrogen is introduced during step (i) and/or step (iii) in a stoichiometric mole ratio.
step (ii) is performed in the presence of hydrogen, preferably with an $H_2$/product to be reacted mole ratio of between 0.3 and 30, especially between 0.5 and 20 and advantageously between 1 and 10, and step (iv) is performed in the absence of hydrogen.
step (ii) is performed in the presence of hydrogen, preferably with an $H_2$/product to be reacted mole ratio of between 0.3 and 30, especially between 0.5 and 20 and advantageously between 1 and 10, and step (iv) is performed in the presence of hydrogen, preferably with an $H_2$/product to be reacted mole ratio of between 0.3 and 30, especially between 0.5 and 20 and advantageously between 1 and 10.
the total amount of hydrogen is introduced during step (i).
the $H_2$/hexafluoropropylene mole ratio is between 2.3 and 30 and advantageously between 3 and 20.
the $H_2$/hexafluoropropylene mole ratio is about 2.
the 1,1,1,2,3,3-hexafluoropropane that has not reacted during step (ii) is separated out after step (ii) or after step (iii), but before step (iv), and is optionally recycled into step (ii) and/or into step (i).
the 1,1,1,2,3,3-hexafluoropropane that has not reacted during step (ii) is not separated out before steps (iii) and (iv), additional 1,2,3,3,3-pentafluoro-1-propene is obtained during step (iv) from the unreacted 1,1,1,2,3,3-hexafluoropropane and this additional 1,2,3,3,3-pentafluoro-1- propene is then separated out and optionally recycled into step (iii) and/or optionally step (ii).

the hydrogenation steps (i) and (iii) are performed in the same reactor, preferably with the same catalyst, a separation step optionally being present.

the dehydrofluorination steps (ii) and (iv) are performed in the same reactor, preferably with the same catalyst, and in which the process also comprises a separation step for separating the products obtained from said reactor, especially as a fraction containing the 2,3,3,3-tetrafluoro-1-propene.

the stream from step (ii) containing the 1,2,3,3,3-pentafluoro-1-propene is sent directly without separation into step (iii) during which the hydrogenation is performed.

steps (i), (ii) and (iii) are performed in the same reactor, on different catalyst beds.

steps (i), (ii) and (iii) are performed in three reactors immediately in series without intermediate separation.

after this step (iii), a separation is performed, and a stream of 1,1,1,2,3,3-hexafluoropropane and optionally of HF is recovered, and is recycled into the start of the process, and a stream of 1,1,1,2,3-pentafluoropropane and optionally of hydrogen, which are sent into step (iv), is recovered.

DETAILED DESCRIPTION OF EMBODIMENTS

The invention uses four reactions in series, employed continuously, in the gas phase, the reaction products being sent into the next step, optionally after having undergone a treatment, for example of separation, if necessary.

In the process, the reaction steps are performed continuously on streams in the gas phase. An economical process for preparing the compound 1234yf is thus obtained, the starting material, HFP, being readily commercially available, at low cost.

The hydrogenation steps are performed in a conventional manner for a person skilled in the art. A person skilled in the art may select the operating conditions so that the reactions are substantially quantitative.

The catalysts that may be used in these reactions are those that are known for this purpose. Mention may be made especially of catalysts based on a group VIII metal or rhenium. This catalyst may be supported, for example on charcoal, alumina, aluminum fluoride, etc., or may not be supported, for instance Raney nickel. As metal, it is possible to use platinum or palladium, in particular palladium, advantageously supported on charcoal or alumina. This metal may also be combined with another metal, for instance silver, copper, gold, tellurium, zinc, chromium, molybdenum or thallium. These hydrogenation catalysts are known.

The catalyst may be present in any suitable form, for example in the form of a fixed or fluidized bed, preferably as a fixed bed. The direction of flow may be downward or upward. The catalyst bed may also comprise a particular distribution of the catalyst so as to control the flows of heat generated by the exothermic reaction. Thus, it is possible to envision charge density, porosity, etc. gradients of the catalyst so as to control the exothermicity of the reaction. For example, it may be envisioned for the first part of the bed to comprise less catalyst, whereas the second part comprises more.

Steps for regenerating the catalyst, in a known manner, may also be envisioned.

It may also be envisioned to use a dilution gas such as nitrogen.

The hydrogenation steps are exothermic. The reaction temperature may be controlled with the aid of means provided for this purpose in the reactor, if necessary. The temperature may vary by a few tens of degrees during the reaction, reaction (i) being more exothermic than reaction (iii). For example, the entry temperature may range from 20° C. to 150° C., and the gain in temperature may range from 5° C. to 100° C.

The contact time (ratio between the volume of catalyst and the total charge flow) is generally between 0.1 and 100 seconds, preferably between 1 and 50 seconds and advantageously between 2 and 10 seconds.

The amount of hydrogen injected may vary within a wide range. The $H_2$/charge ratio may vary within a wide range, especially between 1 (the stoichiometric amount) and 30, especially between 1.5 and 20 and advantageously between 3 and 10. A high ratio will lead to dilution, and thus to better management of the reaction exothermicity.

The dehydrofluorination reactions are also performed in a conventional manner for a person skilled in the art.

The dehydrofluorination reaction may be performed by passage through a basic solution, especially of KOH.

The dehydrofluorination reaction is preferably performed with a dehydrofluorination catalyst. This catalyst is, for example, a catalyst based on a metal, especially a transition metal or an oxide, halide or oxyhalide derivative of such a metal. Catalysts are, for example, $FeCl_3$, chromium oxyfluoride, Ni (including Ni mesh lattices), $NiCl_2$, $CrF_3$, and mixtures thereof. Other possible catalysts are catalysts supported on charcoal, antimony-based catalysts, aluminum-based catalysts (such as $AlF_3$ and $Al_2O_3$ and aluminum oxyfluoride and fluorinated alumina), palladium, platinum, rhodium and ruthenium. Reference may be made to the list given in document U.S. Pat. No. 5,396,000, column 1, line 50 to column 2, line 2 or to the list given in WO 2007/056 194, page 16, lines 13-23.

According to one variant, a mixed catalyst is used.

This catalyst contains both chromium and nickel. The Cr:Ni mole ratio, relative to the metallic element, is generally between 0.5 and 5, for example between 0.7 and 2, and especially in the region of 1. The catalyst may contain, on a weight basis, from 0.5% to 20% of chromium and from 0.5% to 20% of nickel, and preferably between 2% and 10% of each of the metals.

The metal may be present in metallic form or in the form of derivatives, especially oxide, halide or oxyhalide, these derivatives, especially halide and oxyhalide, being obtained via activation of the catalytic metal. Although activation of the metal is not necessary, it is preferred.

The support is based on aluminum. Several possible supports may be mentioned, for instance alumina, activated alumina or aluminum derivatives. These aluminum derivatives are especially aluminum halides or oxyhalides, described, for example, in U.S. Pat. No. 4,902,838, or obtained via the activation process described below.

The catalyst may comprise the chromium and nickel in unactivated form or in activated form, on a support that has also undergone the activation of the metal, or otherwise.

The catalyst may be prepared from alumina (in general an "activated" alumina; this activated alumina is an alumina of high porosity, and is different than the alumina that has undergone the metal activation treatment). In a first step, the alumina is transformed into aluminum fluoride or into a mixture of aluminum fluoride and alumina, by fluorination using air and hydrofluoric acid, the degree of conversion of the alumina into aluminum fluoride depending essentially on the temperature at which the fluorination of the alumina is performed (in general between 200° C. and 450° C. and preferably between 250° C. and 400° C.) The support is then impregnated using aqueous solutions of chromium and nickel salts or using aqueous solutions of chromic acid, nickel salt and methanol (serving as chromium-reducing agent). The chromium and nickel salts that may be used include the chlorides, or other salts, for instance the oxalates, formates, acetates, nitrates and sulfates or nickel dichromate, provided that these salts are soluble in the amount of water that may be absorbed by the support. The catalyst may also be prepared via direct impregnation of alumina (which in general is activated) with the aid of solutions of the chromium and nickel compounds mentioned above. In this case, the conversion of at least part (for example 70% or more) of the alumina into aluminum fluoride or aluminum oxyfluoride is performed during the step of activation of the metal of the catalyst.

The activated aluminas that may be used for the preparation of the catalyst are well-known commercially available products. They are generally prepared by calcination of alumina hydrates (aluminum hydroxides) at a temperature of between 300° C. and 800° C. The aluminas (activated or unactivated) may contain large amounts (up to 1000 ppm) of sodium, without this harming the catalytic performance.

Preferably, but without this being necessary, the catalyst is conditioned or activated, i.e. converted into constituents that are active and stable (under the reaction conditions), via a preliminary "activation" operation. This treatment may be performed either "in situ" (in the dehydrofluorination reactor) or in suitable apparatus designed to withstand the activation conditions.

This activation step generally comprises the following steps:
- A drying step. This drying step is performed at high temperature (250° C. to 450° C. and preferably 300° C. to 350° C.) in general under a stream of nitrogen or air. This step may be optionally preceded in a first stage by a first step of drying at low temperature (100° C. to 150° C. and preferably 110° C. to 120° C.) in the presence of air or nitrogen. The duration of the drying step may be between 10 and 50 hours.
- A fluorination step. This fluorination step is performed at low temperature (180° C. to 350° C.) using a mixture of hydrofluoric acid and nitrogen, while controlling the HF content so that the temperature does not exceed 350° C. The duration of the fluorination step may be between 10 and 50 hours.
- Optionally, a finishing step under a stream of pure hydrofluoric acid or hydrofluoric acid diluted with nitrogen, at a temperature that may be up to 450° C. The duration of the finishing step may be between 2 and 15 hours.

During this operation, the catalytic precursors (for example nickel and chromium halides, nickel chromate or dichromate, chromium oxide) are converted into the corresponding fluorides and/or oxyfluorides, which results in a release of water and/or of hydrochloric acid. Chemical analysis of the elements (chromium, nickel, fluorine, aluminum, oxygen), after this activation, makes it possible to confirm the mineral composition of the catalyst.

Such a catalyst is described in EP-A-486 333, in particular on page 3, lines 11-48, Examples 1A, 2A and 4A, to which passages reference is made.

The dehydrofluorination steps are performed at temperatures that may be between 150° C. and 600° C., preferably between 300 and 500° C. and advantageously between 300 and 450° C., especially between 300 and 400° C.

The contact time (ratio between the volume of catalyst and the total charge flow) is generally between 0.1 and 100 seconds, preferably between 1 and 50 seconds and advantageously between 2 and 20 seconds in the case of the reaction leading to 1234yf, and between 5 and 40 seconds in the case of the reaction leading to 1225ye.

A diluent gas (nitrogen, helium or argon) may be used in the reaction. The pressure in the various reactions may be atmospheric, or lower or higher than this atmospheric pressure. The pressure may vary from one reaction to another, where appropriate.

The reactions are performed in one or more reactors devoted to reactions involving halogens. Such reactors are known to those skilled in the art, and may comprise linings based, for example, on Hastelloy®, Inconel®, Monel® or fluoropolymers. The reactor may also comprise heat-exchange means, if necessary.

In the case where hydrogen is used in excess in the hydrogenation step prior to the dehydrofluorination step, hydrogen will be present during the dehydrofluorination. It may also be envisioned to inject hydrogen into this step (ii), without, however, this hydrogen originating from step (i). The $H_2$/dehydrofluorination charge ratio may vary within a wide range, especially between 0.3 and 30, especially between 0.5 and 20 and advantageously between 1 and 10.

This presence of hydrogen makes it possible to obtain greater selectivity toward the desired product; preferably more stable selectivity over time. Similarly, the formation of heavy fractions is preferably reduced. In the presence of hydrogen, the selectivity is very high toward the desired product, 1225ye or 1234yf, this selectivity preferably being stable over time.

Specifically, for the two dehydrofluorination reactions, the starting material may be represented by formula (I), $CF_3$—CHF—CHFX, in which X is hydrogen or fluorine. Thus, the starting material may correspond to formula (Ia) $CF_3$—CHF—$CHF_2$ (F236ea) or to formula (Ib) $CF_3$—CHF—$CH_2F$ (F245eb). In these two cases, the removal of HF in formula I may lead to two products, the first of formula (II) $CF_3$—CF=CHX and the second of formula (III) $CF_3$—CH=CFX, depending on the fluorine that is removed. There is thus a selectivity problem during the removal of HF from the molecule of the product of formula (I). Such a selectivity problem does not arise if the starting material does not contain fluorine on the terminal carbon intended to bear the double bond, as, for example, F245cb, which can lead only to 1234yf by removal of HF.

When the starting material is the product of formula (Ia) (236ea), the desired product corresponds to formula (IIa), i.e. $CF_3$—CF=CHF (1225ye), whereas the undesired product corresponds to formula (IIIa), the i.e. $CF_3$—CH=$CF_2$ (1225zc).

When the starting material is the product of formula (Ib) (245eb), the desired product corresponds to formula (IIb), i.e. $CF_3$—CF=$CH_2$ (1234yf), whereas the undesired product corresponds to formula (IIIb), i.e. $CF_3$—CH=CHF (1234ze).

The selectivity toward product of formula (II), whether it is (IIa) or (IIb), is very high, greater than 90%, preferably greater than 95% and even advantageously greater than or equal to 98%.

The conversion is also very high. Advantageously, the conversion is stable over time.

The reagents are generally fed in continuously, or may be fed in stages, where appropriate. The points for the possible separation and/or recycling operations are variable, at the start of the process or at intermediate levels.

According to one embodiment, hydrogen is present during the dehydrofluorination step (ii). This hydrogen may be injected during this step, or may originate from an excess of hydrogen used in the first step, which is not separated out before step (ii). According to one embodiment, hydrogen is introduced in excess into the first reaction, and it is kept during the first dehydrohalogenation step (ii) and optionally up to the final step (iv) which corresponds to the second dehydrofluorination; this step (iv) may also be performed in the absence of hydrogen. For example, the total amount of hydrogen used in the process is introduced during step (i), the $H_2$/hexafluoropropylene mole ratio being between 2.3 and 30 and advantageously between 3 and 20. In such a case, and on the basis of the low value of the mole ratio of 2.3 mol of hydrogen per one mole of HFP, 1.3 mol of hydrogen remains during the first dehydrofluorination step (which promotes the selectivity, advantageously stably over time) and the $H_2$/pentafluoropropylene ratio is then 1.3 (accepting that the conversion and the selectivity of the first dehydrofluorination step is quantitative). One mole of hydrogen is consumed during the hydrogenation reaction toward 245eb, and 0.3 mol of hydrogen thus remains for the second dehydrofluorination step (which again promotes the selectivity). It is also possible for the amount of hydrogen to be such that it is in a mole ratio of about 2, such that all the hydrogen is consumed and that the last reaction (iv) is performed in the absence of hydrogen (if step (ii) is quantitative).

The hydrogen mole ratios are expressed on the basis of quantitative reactions (especially for the dehydrohalogenation reactions and in particular reaction (ii); the hydrogen mole ratios are recalculated as a function of the conversion and the selectivity toward the desired product).

The hydrogen may also be introduced in stages, additional hydrogen being introduced before the second hydrogenation or before each dehydrofluorination step if it is desired for these steps to be performed in the presence of hydrogen. Thus, the first hydrogenation step may be performed with an $H_2$/hexafluoropropylene mole ratio of 1.5, and the remaining excess hydrogen (about 0.5 mol of hydrogen per one mole of HFP) is kept in step (ii) of the first dehydrofluorination. Before this step or immediately after this step, it is possible to add hydrogen in order for the ratio $H_2$:1225ye to be at least equal to 1 and advantageously greater than 1 (in order for the final dehydrofluorination step (iv) to be performed in the presence of hydrogen to improve the selectivity). Hydrogen may also be added to the reaction medium before each step, if desired. It is possible for the dehydrofluorination step (ii) to be performed in the presence of hydrogen, whereas the final step (iv) is not performed in the presence of hydrogen.

The hydrogen that has not been consumed in one or more steps is advantageously separated out and recycled into the process, advantageously into the start of the process.

The hydrogenation reactions are preferably substantially quantitative. The dehydrofluorination reactions are not necessarily always quantitative; in particular, reaction (ii) for formation of 1225ye is not necessarily quantitative, and unreacted 236ea may remain.

This the unreacted compound 236ea may be separated out, either after step (ii) or after step (iii) (but before step (iv)). Advantageously, the separation takes place after step (iii), the boiling points of 236ea and of 245eb being, respectively, 6° C. and 22.7° C., and thus having a difference of more than 15° C. The separation may take place at these two moments since the hydrogenation reaction (iii) does not substantially affect 236ea. This 236ea separated out may be recycled into the process. It may be recycled into step (ii) during which it reacts. It may also be recycled into the start of the process, in step (i), and serve as diluent during this step. The diluent action of 236ea makes it possible to control the exothermicity of the first hydrogenation reaction.

This unreacted compound 236ea may also not be separated out and may remain in the process, especially up to step (iv). During this dehydrofluorination step (iv), additional 1,2,3,3,3-pentafluoro-1-propene (1225ye) will then be formed from the unreacted 236ea. The two compounds 1225ye and 1234yf may then be separated and the 1225ye recycled. The boiling points of the two fluoroolefins are, admittedly, similar, but it is possible to achieve separation of these two compounds. The recycling may be performed into step (ii) and/or into step (iii). This 1225ye will be quantitatively converted during the hydrogenation reaction of step (iii), which is substantially quantitative.

It is thus possible to control the product flows in the process according to the invention as a function of the possible separation needs. The HF that is formed may be separated out after each dehydrofluorination reaction, either between these two reactions, or only at the end of the process. The HF may be separated out by washing or by distillation. The azeotropes that may be formed with HF may also be separated out after the step during which they are formed, or after a subsequent step or at the end of the process. These separation steps are thus placed in the process as a function of the various needs. It is also possible to envision recycling of only certain separated compounds (for example the unreacted 236ea), whereas the other separated components are sent toward other processes.

Advantageously, the 1,2,3,3,3-pentafluoro-1-propene (1225ye) is not separated out, which avoids the handling of this toxic product. It is possible to send the stream from step (ii) directly into the following step.

For example, the process may be one in which steps (i), (ii) and (iii) are performed in the same reactor, on different catalyst beds. Advantageously, in this case, after step (iii), a separation and optional removal of HF is performed, a stream of 1,1,1,2,3,3-hexafluoropropane is recovered, which is recycled into the start of the process, and a stream of 1,1,1,2,3-pentafluoropropane and optionally (but preferably) of hydrogen is recovered and sent into step (iv). The 1,2,3,3,3-pentafluoro-1-propene (1225ye) is not separated out since it is converted in the reactor into 245eb, which avoids the handling of this toxic product 1225ye. Three reactors directly in series may also be envisioned, the stream leaving one reactor being sent directly into the next reactor without separation.

In the case targeted above of a single reactor, the reactor may contain three different catalytic species, with different functions. The hydrogenation of the HFP is performed on a first catalytic bed (total conversion and virtually 100% selectivity). The 236ea and the excess hydrogen then pass through a second catalytic bed, at a suitable temperature (the heating may be electric, for example). The reaction products are then 1225ye, HF, excess hydrogen and possibly unreacted 236ea. These are then sent through a third catalytic bed in which a hydrogenation takes place (total conversion and virtually 100% selectivity).

In the above cases of a single reactor or of three reactors immediately in series, an outlet stream is then obtained containing 245eb, possibly excess hydrogen, HF possibly with azeotropes, and possibly the unreacted 236ea present before the hydrogenation step. The hydrogen is separated out, and is recycled into the top of the reactor (or into another level in the process) and the 236ea is separated from the 245eb. The 236ea may also be recycled into the reactor inlet. The HF and optionally the azeotropes are also separated out (optionally partly by washing).

It is also possible in the process to envisage that the hydrogenation steps (i) and (iii) be performed in the same reactor, preferably with the same catalyst, and/or that the dehydrofluorination steps (ii) and (iv) be performed in the same reactor, preferably with the same catalyst. WO 2007/117 391 describes the co-dehydrofluorination of 236ea and of 245eb to produce a mixture of 1225ze and 1234yf. These two compounds are not separated after that process.

The co-hydrogenation is performed in a first reactor, the outlet stream of which contains 236ea and 245eb. The outlet stream may be separated, and the 236ea is sent into a first dehydrofluorination reactor, whereas the 245eb is sent into a second dehydrofluorination reactor. The outlet stream from the first dehydrofluorination reactor predominantly contains 1225ye and possibly unreacted 236ea. The outlet stream from the first dehydrofluorination reactor may be sent to the hydrogenation reactor, thus producing compound 245eb from this 1225ye. The 236ea optionally separated out may be recycled into the top of this dehydrofluorination reactor.

The process may also be performed by sending the outlet stream from the hydrogenation reactor (containing 245eb and 236ea) or the combination of the two streams from the two hydrogenation reactors may be sent directly into a single dehydrofluorination reactor. The stream from this dehydrofluorination reactor contains 1234yf, but also unreacted 236ea and 1225ye resulting from the dehydrofluorination of 236ea. This stream is separated and the 1234yf, 1225ye and 236ea are recovered. As indicated above, the two fluoroolefins may be separated. It is possible for the 236ea to be recycled into the top of the dehydrofluorination reactor, whereas the stream of 1225ye is recycled into the top of the hydrogenation reactor. It is also possible to recycle these two compounds into the top of the hydrogenation reactor(s).

It will be recalled that:
the degree of conversion is the percentage of starting material that has reacted (number of moles of reacted starting material/number of moles of starting material introduced);
the selectivity toward the desired product is the ratio of the number of moles of desired product formed/number of moles of starting material that has reacted;
the yield of desired product is the ratio of the number of moles of desired product formed/number of moles of starting material introduced, the yield of desired product also possibly being defined as the product of the conversion and of the selectivity.
the contact time is the inverse of the gas hourly space velocity (GHSV)
the space velocity is the ratio between the total volume throughput of the gaseous stream to the volume of the catalytic bed, under normal temperature and pressure conditions.
the productivity is expressed as mass of desired product obtained per unit time and per unit of catalyst (mass or volume); this productivity is linked to the contact time.

EXAMPLES

The examples that follow illustrate the invention without limiting it.

Example 1

The Hydrogenation of HFP to 236ea

A reactor containing 10 g of catalyst in the form of a 16 cm$^3$ fixed bed is used. The catalyst is a catalyst of the 2% Pd/C pellet type. The pressure is 1 bar.

The following results are then obtained (MR means mole ratio).

| Temp. | Contact time | MR H$_2$/HFP | Conversion | Selectivity 236ea | Organic impurities | Productivity 236ea h/m$^3$ cata |
|---|---|---|---|---|---|---|
| 120° C. | 3.8 sec | 5 | 100% | 99% | 0.8 | 1050 |

Example 2

Dehydrofluorination of 236ea to 1225ye

Preparation of the Dehydrofluorination Catalyst.

The catalyst used is an Ni—Cr/AlF$_3$ catalyst, which is prepared as follows.

343 g of a support obtained in a preceding step by fluorination of Grace HSA alumina are placed in a rotary evaporator as a fixed bed at about 280° C. using air and hydrofluoric acid (volume concentration of 5% to 10% of this acid in air). The Grace HSA starting alumina has the following physicochemical characteristics:

| | |
|---|---|
| Form | beads 0.5-2 mm in diameter |
| BET surface area | 220 m$^2$/g |
| pore volume | 1.3 cm$^3$/g |

Separately, two separate aqueous solutions are prepared:
(a) chromic solution supplemented with nickel chloride containing:

| | |
|---|---|
| chromium trioxide | 55 g |
| nickel chloride hexahydrate | 130 g |
| water | 63 g |

(b) Methanolic solution containing:

| | |
|---|---|
| methanol | 81 g |
| water | 8 g |

These two solutions are introduced simultaneously at a temperature of 40° C. at atmospheric pressure and over about 2 hours onto the support with stirring. After a maturation step under nitrogen, the catalyst is dried under nitrogen, and then under vacuum at 65° C., and then at about 90° C. for 6 hours.

500 g of impregnated solid are placed in an Inconel tubular reactor. The catalyst is first dried under a stream of nitrogen at low temperature and then up to 320° C., at atmospheric pressure. It is then fluorinated in the presence of a hydrofluoric acid/nitrogen mixture (volume concentration of 5% to 10% of this acid in nitrogen) at 320° C. and then up to 390° C. The HF feed is then stopped. Flushing with nitrogen is continued for 15 minutes at 390° C. and the catalyst is then cooled to 60° C. under a stream of nitrogen.

The characteristics of the catalyst after activation are as follows:

| | |
|---|---|
| BET surface area | 40 m$^2$/g |
| pore volume | 0.4 cm$^3$/g |

-continued

| chemical composition by weight: | |
|---|---|
| Al | 25% |
| F | 58% |
| Cr | 5.3% |
| Ni | 6.4% |

A reactor containing 20 g of catalyst in the form of a 23 cm³ fixed bed is used. The pressure is 1 bar.

The following results are then obtained (MR means mole ratio).

| Temp. | Contact time | MR $H_2$/236ea | Conversion | Selectivity 1225ye | Ratio Z/E | Productivity 1225ye h/m³ cata |
|---|---|---|---|---|---|---|
| 375° C. | 6.6 sec | 4.05 | 49.5% | 98% | 7.3 | 310 |

Example 3

Hydrogenation of 1225ye to 245eb

A reactor containing 10 g of catalyst (identical to that used in Example 1) in the form of a 16 cm³ fixed bed is used. The pressure is 1 bar.

The following results are then obtained (MR means mole ratio).

| Temp. | Contact time | MR $H_2$/1225 | Conversion | Selectivity 236ea | Organic impurities | Productivity 245eb h/m³ cata |
|---|---|---|---|---|---|---|
| 20/60° C. | 4.6 sec | 8.5 | 100% | 99.5% | 0.5 | 450 |

Example 4

Dehydrofluorination of 245eb to 1234yf

A reactor containing 10 g of catalyst (identical to that used in Example 2) in the form of a 12 cm³ fixed bed is used. The pressure is 1 bar.

The following results are then obtained (MR means mole ratio).

| Temp. | Contact time | MR $H_2$/245eb | Conversion | Selectivity 1234yf | Selectivity 1234ze | Productivity 1234yf h/m³ cata |
|---|---|---|---|---|---|---|
| 373° C. | 8.9 sec | 3 | 87% | 90% | 9% | 436 |

The invention claimed is:

1. A continuous gas-phase process for preparing 2,3,3,3-tetrafluoro-1-propene, comprising the following steps:
    (i) hydrogenation of hexafluoropropylene to 1,1,1,2,3,3-hexafluoropropane;
    (ii) dehydrofluorination of the 1,1,1,2,3,3-hexafluoropropane obtained in the preceding step to 1,2,3,3,3-pentafluoro-1-propene;
    (iii) hydrogenation of the 1,2,3,3,3-pentafluoro-1-propene obtained in the preceding step to 1,1,1,2,3-pentafluoropropane;
    (iv) dehydrofluorination of the 1,1,1,2,3-pentafluoropropane obtained in the preceding step to 2,3,3,3-tetrafluoro-1-propene.

2. The process as claimed in claim 1, in which hydrogen is introduced during step (i) and/or step (iii) in a stoichiometric mole ratio.

3. The process as claimed in claim 1, in which step (ii) is performed in the presence of hydrogen, with an $H_2$/product to be reacted mole ratio of between 0.3 and 30, and step (iv) is performed in the absence of hydrogen.

4. The process as claimed in claim 1, in which step (ii) is performed in the presence of hydrogen, with an $H_2$/product to be reacted mole ratio of between 0.3 and 30, and step (iv) is performed in the presence of hydrogen, with an $H_2$/product to be reacted mole ratio of between 0.3 and 30.

5. The process as claimed in claim 1, in which hydrogen is introduced only during step (i).

6. The process as claimed in claim 5, in which the $H_2$/1,1,1,2,3,3-hexafluoropropylene mole ratio is between 2.3 and 30.

7. The process as claimed in claim 5, in which the $H_2$/1,1,1,2,3,3-hexafluoropropylene mole ratio is about 2.

8. The process as claimed in claim 1, in which the 1,1,1,2,3,3-hexafluoropropane that has not reacted during step (ii) is separated out after step (ii) or after step (iii), but before step (iv), and is optionally recycled into step (ii) and/or into step (i).

9. The process as claimed in claim 1, in which 1,1,1,2,3,3-hexafluoropropane that has not reacted during step (ii) is not separated out before steps (iii) and (iv), additional 1,2,3,3,3-pentafluoro-1-propene is obtained during step (iv) from unreacted 1,1,1,2,3,3-hexafluoropropane and said additional 1,2,3,3,3-pentafluoro-1-propene is separated out and optionally recycled into step (iii) and/or step (ii).

10. The process as claimed in claim 1, in which the hydrogenation steps (i) and (iii) are performed in the same reactor, preferably with the same catalyst, a separation step optionally being present.

11. The process as claimed in claim 1, in which the dehydrofluorination steps (ii) and (iv) are performed in the same reactor, preferably with the same catalyst, and in which the process further comprises a separation step for separating the products obtained from said reactor, as a fraction containing 2,3,3,3-tetrafluoro-1-propene.

12. The process as claimed in claim 1, in which the stream from step (ii) containing 1,2,3,3,3-pentafluoro-1-propene is sent directly, without separation, into step (iii) during which hydrogenation takes place.

13. The process as claimed in claim 1, in which steps (i), (ii) and (iii) are performed in the same reactor, on different catalyst beds.

14. The process as claimed in claim 1, in which steps (i), (ii) and (iii) are performed in three reactors in series without intermediate separation.

15. The process as claimed in claim 13, in which, after step (iii), separation is performed, a stream of 1,1,1,2,3,3-hexafluoropropane and optionally of HF is recovered, and is recycled into the start of the process, and a stream of 1,1,1,2,3-pentafluoropropane and optionally of hydrogen, is recovered and sent into step (iv).

16. The process as claimed in claim 3, in which the $H_2$/product to be reacted mole ratio is between 0.5 and 20.

17. The process as claimed in claim 3, in which the $H_2$/product to be reacted mole ratio is between 1 and 10.

18. The process as claimed in claim 4, in which the $H_2$/product to be reacted mole ratio is between 0.5 and 20.

19. The process as claimed in claim 4, in which the $H_2$/product to be reacted mole ratio is between 1 and 10.

20. The process as claimed in claim 5, in which the $H_2$/1,1,1,2,3,3-hexafluoropropylene mole ratio is between 3 and 20.

21. The process as claimed in claim 4, in which, after step (iii), a separation is performed, a stream of 1,1,1,2,3,3-hexafluoropropane and optionally of HF is recovered, and is recycled into the start of the process, and a stream of 1,1,1,2,3-pentafluoropropane and optionally of hydrogen, is recovered and sent into step (iv).

* * * * *